x

US007785630B2

(12) United States Patent
Dietrich et al.

(10) Patent No.: US 7,785,630 B2
(45) Date of Patent: Aug. 31, 2010

(54) PREPARATION AND ADMINISTRATION FORM COMPRISING AN ACID-LABILE ACTIVE COMPOUND

(75) Inventors: Rango Dietrich, Constance (DE); Rudolf Linder, Constance (DE)

(73) Assignee: NYCOMED GmbH, Constance (DE)

( * ) Notice: Subject to any disclaimer, the term of this patent is extended or adjusted under 35 U.S.C. 154(b) by 0 days.

(21) Appl. No.: 11/980,572

(22) Filed: Oct. 31, 2007

(65) Prior Publication Data

US 2008/0069882 A1   Mar. 20, 2008

Related U.S. Application Data

(63) Continuation of application No. 09/980,492, filed as application No. PCT/EP00/04958 on May 31, 2000.

(30) Foreign Application Priority Data

Jun. 7, 1999   (EP)   ................... 99110865

(51) Int. Cl.
*A61K 9/14* (2006.01)
*A61K 9/48* (2006.01)
*A61K 9/20* (2006.01)
*A61K 9/46* (2006.01)

(52) U.S. Cl. .................. 424/489; 424/451; 424/464; 424/466

(58) Field of Classification Search .............. None
See application file for complete search history.

(56) References Cited

U.S. PATENT DOCUMENTS

| 3,065,142 | A | | 11/1962 | Antonides |
| 3,800,038 | A | | 3/1974 | Rudel |
| 4,637,996 | A | * | 1/1987 | Konishi ............... 514/11 |
| 4,755,385 | A | | 7/1988 | Etienne et al. |
| 4,758,579 | A | | 7/1988 | Kohl et al. |
| 4,818,760 | A | | 4/1989 | Binder et al. |
| 4,845,118 | A | | 7/1989 | Lang et al. |
| 4,876,094 | A | * | 10/1989 | Benton et al. ............. 424/491 |
| 5,023,089 | A | | 6/1991 | Sakamoto et al. |
| 5,183,493 | A | | 2/1993 | Brandau et al. |
| 5,213,810 | A | | 5/1993 | Steber |
| 5,456,920 | A | | 10/1995 | Matoba et al. |
| 5,772,187 | A | | 6/1998 | Wirodihardjo et al. |
| 5,948,773 | A | | 9/1999 | Akiyama et al. |
| 5,972,389 | A | | 10/1999 | Shell et al. |
| 6,120,803 | A | | 9/2000 | Wong et al. |
| 6,174,548 | B1 | | 1/2001 | Chen et al. |
| 6,328,993 | B1 | | 12/2001 | Linder et al. |
| 6,423,869 | B1 | * | 7/2002 | Miyagawa et al. ......... 562/553 |
| 6,582,720 | B1 | * | 6/2003 | Inagi et al. ............... 424/434 |
| 6,632,457 | B1 | | 10/2003 | Sawhney |

| 2003/0157177 | A1 | 8/2003 | Langlois et al. |

FOREIGN PATENT DOCUMENTS

| DE | 27 25 924 | 12/1978 |
| EP | 0 005 129 | 10/1979 |
| EP | 0 031 134 A2 | 7/1981 |
| EP | 0 166 287 A1 | 1/1986 |
| EP | 0 174 726 | 3/1986 |
| EP | 0 184 322 B1 | 6/1986 |
| EP | 0 208 971 | 1/1987 |
| EP | 0 234 485 B1 | 9/1987 |
| EP | 0 244 380 | 11/1987 |
| EP | 0 268 956 | 1/1988 |
| EP | 0 261 478 B1 | 3/1988 |
| EP | 0 277 741 | 8/1988 |
| EP | 0 342 522 | 11/1989 |
| EP | 0 351 580 | 1/1990 |
| EP | 0 434 999 B1 | 7/1991 |
| EP | 0 467 221 B1 | 1/1992 |
| EP | 0 514 008 | 11/1992 |
| EP | 0 519 365 | 12/1992 |
| FR | 2 754 177 | 4/1998 |
| GB | 2 112 389 | 7/1983 |
| GB | 2 163 747 A | 3/1986 |
| JP | 2000-86502 | 3/2000 |
| WO | 91/19710 A1 | 12/1991 |

(Continued)

OTHER PUBLICATIONS

Lewis, L., et al., "The physical and chemical stability of suspensions of sustained-release diclofenac microspheres", *J. Microencapsulation*, vol. 15, No. 5, pp. 555-567, (1998).

(Continued)

*Primary Examiner*—Humera N Sheikh
(74) *Attorney, Agent, or Firm*—The Nath Law Group; Joshua B. Goldberg; Sheldon M. McGee

(57) ABSTRACT

Novel administration forms and preparation for acid-labile active compounds are described. The novel administration forms contain individual active compound units, the active compound being present in the active compound units in a matrix made of a mixture comprising at least one fatty alcohol and at least one solid paraffin, in a matrix made of a mixture of a triglyceride and at least one solid paraffin or in a matrix made of a mixture comprising at least one fatty acid ester and at least one solid paraffin. In particular, the active compound units are microspheres which can be produced by prilling.

18 Claims, No Drawings

FOREIGN PATENT DOCUMENTS

| | | |
|---|---|---|
| WO | 95/28226 A1 | 10/1995 |
| WO | 96/01623 | 1/1996 |
| WO | 96/01624 | 1/1996 |
| WO | 96/01625 | 1/1996 |
| WO | 97/25030 | 7/1997 |
| WO | 98/15268 A1 | 4/1998 |
| WO | 98/52564 | 11/1998 |
| WO | 99/29299 | 6/1999 |
| WO | 99/29320 | 6/1999 |
| WO | 99/33555 | 7/1999 |
| WO | 99/48498 A1 | 9/1999 |
| WO | 00/24382 | 5/2000 |

OTHER PUBLICATIONS

Adeyeye, C.M, et al., "Development and Evaluation of Sustained-Release Ibuprofen-Wax Microspheres. I. Effect of Formulation Variables on Physical Characteristics", *Pharmaceutical Research*, vol. 8, No. 11, pp. 1377-1383, (1991).

Derwent Publications AN 1993-348343, abstract of JP 05-255074 (Dec. 3, 1992).

* cited by examiner

PREPARATION AND ADMINISTRATION FORM COMPRISING AN ACID-LABILE ACTIVE COMPOUND

This application is a continuation application of U.S. Ser. No. 09/980,492, filed Dec. 4, 2001, which was filed under 35 U.S.C. 371 as a national stage of PCT/EP00/04958, filed May 31, 2000.

TECHNICAL FIELD

The present invention relates to the field of pharmaceutical technology and describes a novel administration form comprising an acid-labile active compound, in particular an acid-labile proton pump inhibitor. Furthermore, the invention also relates to processes for the production of the administration form, preparations which can be used for the production of the administration form, and a process for the production of the preparations.

PRIOR ART

It is generally known to coat peroral administration forms, e.g. tablets or pellets which contain an acid-labile active compound, with an enteric coating which, after passage through the stomach, rapidly dissolves in the alkaline medium of the intestine. Examples of such acid-labile active compounds are acid-labile proton pump inhibitors ($H^+/K^+$ ATPase inhibitors), in particular pyridin-2-ylmethylsulfinyl-1H-benzimidazoles, such as are disclosed, for example, in EP-A-0 005 129, EP-A-0 166 287, EP-A-0 174 726 and EP-A-0 268 956. On account of their $H^+/K^+$ ATPase-inhibiting action, these are of importance in the therapy of diseases which are due to increased gastric acid secretion. Examples of active compounds from this group which are already commercially available are 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methylsulfinyl]-1H-benzimidazole (INN: lansoprazole) and 2-{[(4-(3-methoxypropoxy)-3-methylpyridin-2-yl]-methylsulfinyl}-1H-benzimidazole (INN: rabeprazole).

Because of their strong tendency to decompose in a neutral and, in particular, in an acidic environment, where strongly colored decomposition products are also formed, for oral preparations it is also necessary in this case to protect the active compounds from the action of acids. In the case of the strongly acid-labile pyridin-2-ylmethylsulfinyl-1H-benzimidazoles, it is moreover necessary to process these in the tablet core or in pellets in the form of their alkaline salts, for example as sodium salts, or together with alkaline substances. Since the substances suitable for enteric coatings are those having free carboxyl groups, the problem results that the enteric coating is partly dissolved or even dissolved from inside because of the alkaline medium in the interior and the free carboxyl groups promote the decomposition of the active compounds. It is therefore necessary to provide an isolating intermediate layer (subcoating) between the enteric coating and the alkaline tablet core or pellet, it is proposed in EP-A-0 244 380 to coat cores which contain the active compound together with alkaline compounds or as an alkaline salt with at least one layer of nonacidic, inert pharmaceutically acceptable substances, which are soluble in water or rapidly decompose in water, before the enteric layer is applied. The intermediate layer or intermediate layers act as pH-buffering zones in which the hydrogen ions diffusing in from outside can react with the hydroxyl ions diffusing from the alkaline core. In order to increase the buffer capacity of the intermediate layer, it is proposed to incorporate buffer substances into the intermediate layer(s). In practice, it is possible by this process to obtain somewhat stable preparations. However, relatively thick intermediate layers are needed in order to avoid the unsightly discolorations occurring even in the case of only slight decomposition. Moreover, a considerable effort is to be made in the preparation to avoid traces of moisture.

In EP-A-0 519 365, a formulation on the principle of the alkaline core coated with a water-soluble intermediate layer and an enteric coating is proposed for the active compound pantoprazole, in which improved stability is achieved by use of polyvinylpyrrolidone and/or hydroxypropylmethylcellulose as binders for the alkaline core.

EP-A-0 342 522 discloses a formulation for acid-sensitive benzimidazoles in which, between the alkaline core and the enteric coating, an intermediate layer is located which is composed of only slightly water-soluble film-forming material, such as ethylcellulose and polyvinyl acetate, and a slightly water-soluble finely granular inorganic or organic material suspended therein, such as, for example, magnesium oxide, silicon oxide or sucrose fatty acid esters.

EP-A-0 277 741 describes spherical granules having a core which is coated with spray powder, which contains low-substituted hydroxypropylcellulose and a benzimidazole compound having anti-ulcer activity. These granules can be coated with an enteric coating agent.

WO 96/01623, WO 96/01624 and WO 96/01625 describe an administration form for acid-labile $H^+/K^+$ ATPase inhibitors, in which the active compound pellets are compressed together with tablet excipients to give a tablet. The pellets consist of cores which contain the acid-labile.$H^+/K^+$ ATPase inhibitor together with alkaline compounds or as an alkaline salt. The cores of the pellets are coated with one or more layers, at least one layer having enteric properties. In a mechanical respect, the enteric coating must in this case be constituted such that on compression to give tablets the acid resistance of the pellets is not adversely affected. It is mentioned that the production of the cores of the pellets can be carried out by spray drying.

WO 97/25030 describes the processing of the abovementioned pellets to give an effervescent tablet.

WO 98/52564 describes a pharmaceutical composition in pellet form, which has an inert core, a benzimidazole on or in the core, a moisture-resistant layer around the core and an enteric coating over the moisture-resistant layer. Hydrophobic materials such as, for example, cetyl alcohol are mentioned as constituents of the moisture-resistant layer.

EP-A-0 514 008 describes pharmaceutical administration forms for acid-labile benzimidazoles based on a solid matrix of a polyglycerol fatty acid ester or a lipid and the active compound. At least in the vicinity of the matrix surface, a substance is dispersed which develops viscosity on contact with water. It is mentioned that such an administration form can settle in the digestive tract, remains there for a relatively long time and the bioavailability of the active compound is increased.

As the abovementioned prior art shows, the production of peroral administration forms for acid-labile active compounds requires technically complicated processes.

DESCRIPTION OF THE INVENTION

It is the object of the present invention to provide a novel administration form for acid-labile active compounds, which can be prepared without great technical effort and exhibits good controllability of the release of active compound. A further object of the invention is the provision of an administration form in which the acid-labile active compound does not have to be protected by an enteric coating.

It has now surprisingly been found that this object can be achieved by an administration form which contains multiple individual active compound units, the acid-labile active compound being present in the individual active compound units in a matrix made of a mixture of at least one fatty alcohol and at least one solid paraffin, being present in a matrix made of a mixture of at least one triglyceride and at least one solid paraffin or being present in a matrix made of a mixture of at least one fatty acid ester and at least one solid paraffin.

One subject of the invention is therefore an administration form for acid-labile active compounds, comprising pharmaceutical excipients and multiple individual active compound units, wherein the acid-labile active compound is present in the individual active compound units in a matrix made of a mixture comprising at least one fatty alcohol and at least one solid paraffin.

A further subject of the invention is also an administration form for acid-labile active compounds, comprising pharmaceutical excipients and multiple individual active compound units, wherein the acid-labile active compound is present in the individual active compound units in a matrix made of a mixture comprising at least one triglyceride and at least one solid paraffin.

The invention furthermore relates to an administration form for acid-labile active compounds, comprising pharmaceutical excipients and multiple individual active compound units, wherein the acid-labile active compound is present in the individual active compound units in a matrix made of a mixture comprising at least one fatty acid ester and at least one solid paraffin.

Further subjects follow from the patent claims.

The multiple individual active compound units (also described as preparations below) within the meaning of the invention are multiple individual units, in which at least one active compound particle is present in a matrix made of a mixture comprising at least one fatty alcohol and at least one solid paraffin, in a matrix made of a mixture comprising at least one triglyceride and at least one solid paraffin or in a matrix made of a mixture comprising at least one fatty acid ester and at least one solid paraffin. Preferably, the active compound units are microspheres.

The active compound units according to the invention are distinguished in particular by good stability, release of the active compound which can be controlled by means of the particle size, good flow behavior, good compressibility and by a constant (determined by the uniform surface) release of active compound.

The particle size of the individual units is advantageously less than or equal to 2 mm, preferably from 50-800 µm, particularly preferably 50-700 µm and very particularly preferably 50-600 µm. They are preferably microspheres having a particle size of 50-500 µm, particularly preferably of 50-400 µm. They are particularly preferably monomodal microspheres having a particle size of 50-400 µm, particularly preferably of 50-200 µm.

Acid-labile active compounds within the meaning of the present invention are, for example, acid-labile proton pump inhibitors.

Acid-labile proton pump inhibitors ($H^+/K^+$ ATPase inhibitors) within the meaning of the present invention which may be mentioned are in particular substituted pyridin-2-yl-methylsulfinyl-1H-benzimidazoles, such as are disclosed, for example, in EP-A-0 005 129, EP-A-0 166 287, EP-A-0 174 726, EP-A-0 184 322, EP-A-0 261 478 and EP-A-0 268 956. Mention may preferably be made here of 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methylsulfinyl]-1H-benzimidazole (INN: lansoprazole) and 2-{[4-(3-methoxypropoxy)-3-methylpyridin-2-yl]-methylsulfinyl}-1H-benzimidazole (INN: rabeprazole).

Further acid-labile proton pump inhibitors, for example substituted phenylmethylsulfinyl-1H-benzimidazoles, cycloheptapyridin-9-ylsulfinyl-1H-benzimidazoles or pyridin-2-ylmethylsulfinylthienoimidazoles, are disclosed in DE-A-35 31 487, EP-A-0 434 999 and EP-A-0 234 485. Examples which may be mentioned are 2-[2-(N-isobutyl-N-methylamino)benzylsulfinyl]benzimidazole (INN: leminoprazole) and 2-(4-methoxy-6,7,8,9-tetrahydro-5H-cyclohepta[b]pyridin-9-ylsulfinyl)-1H-benzimidazole (INN: nepaprazole).

The acid-labile proton pump inhibitors are chiral compounds. The term acid-labile proton pump inhibitor also includes the pure enantiomers of the acid-labile proton pump inhibitors and their mixtures in any mixing ratio. Pure enantiomers which may be mentioned by way of example are 5-methoxy-2-[(S)-[(4-methoxy-3,5-dimethyl-2-pyridinyl)methyl]sulfinyl]-1H-benzimidazole (INN: esomeprazole) and (–)-pantoprazole.

The acid-labile proton pump inhibitors are present here as such or preferably in the form of their salts with bases. Examples of salts with bases which may be mentioned are sodium, potassium, magnesium and calcium salts. If desired, the salts of the acid-labile proton pump inhibitors with bases can also be present in hydrate form. Such a hydrate of the salt of an acid-labile proton pump inhibitor with a base is disclosed, for example, in WO 91/19710.

Particularly preferred acid-labile proton pump inhibitors which may be mentioned are pantoprazole sodium sesquihydrate (=pantoprazole sodium×1.5 $H_2O$), (–)-pantoprazole sodium sesquihydrate, omeprazole magnesium, omeprazole, esomeprazole magnesium and esomeprazole.

The fatty alcohol is preferably a linear, saturated or unsaturated primary alcohol having 10-30 carbon atoms. It is preferably a primary alcohol having 10 to 18 carbon atoms in linear chains. Fatty alcohols which may be mentioned by way of example are cetyl alcohol, myristyl alcohol, lauryl alcohol or stearyl alcohol, cetyl alcohol being preferred. If desired, mixtures of fatty alcohols can also be present.

The triglyceride is glycerol whose three hydroxyl groups are esterified by carboxylic acids. Preferably, the carboxylic acids are monobasic carboxylic acids having 8 to 22 carbon atoms, preferably naturally occurring carboxylic acids. In this context, they can be different or, preferably, identical carboxylic acids. Examples which may be mentioned are tristearate, tripalmitate and particularly preferably trimyristate (these triglycerides are commercially available under the name Dynasan 118, 116 or 114). If desired, mixtures of triglycerides can also be present.

The fatty acid ester is the ester of an alcohol with a fatty acid. In this case, the alcohol is preferably a linear, saturated or unsaturated primary alcohol having 10-30, preferably having 12 to 18, carbon atoms. The fatty acid is preferably a monobasic carboxylic acid having 8 to 22, in particular 12 to 18, carbon atoms, preferably a naturally occurring carboxylic acid. According to the invention, preferred fatty acid esters are those having a melting point of greater than 30° C. A fatty acid ester which may be mentioned by way of example is cetyl palmitate, which is commercially available, for example, under the name Cutina® CP. If desired, mixtures of fatty acid esters can also be present.

The solid paraffin is preferably paraffinum solidum (paraffin wax). Alternatively, for example, ozocerite can also be used. If desired, mixtures can also be used.

If desired, the mixtures in the individual active compound units can have one or more further pharmaceutically suitable excipients. Examples of further suitable excipients which may be mentioned are polymers, sterols and basic compounds.

Examples of polymers which may be mentioned are povidone (e.g. Kollidon® 17, 30 and 90 from BASF), vinylpyrrolidone/vinyl acetate copolymer and polyvinyl acetate. Mention may furthermore be made of cellulose ethers [such as, for example methylcellulose, ethylcellulose (Ethocel®) and hydroxypropylmethylcellulose], cellulose esters [such as cellulose acetate phthalate (CAP), cellulose acetateltrimellitate (CAT), hydroxypropylmethylcellulose phthalate (HP50 and HP55) or hydroxypropylmethylcellulose acetate succinate (HPMCAS)], methacrylic acid/methyl methacrylate copolymer or methacrylic acid/ethyl methacrylate copolymer (Eudragit® L). The polymer is preferably povidone or ethylcellulose. If desired, mixtures of polymers can also be present. By addition of suitable polymers, it is possible, for example, to influence the properties of the individual active compound units pharmaceutically (e.g. release of the active compound). By addition of suitable polymers such as cellulose acetate phthalate and hydroxypropylmethylcellulose phthalate (HP50 and HP55), a gastric juice resistance (delayed release according to definition of United States Pharmacopeia) of the individual active compound units can be achieved. For the production of an active compound unit having controlled release (extended release according to definition of United States Pharmacopeia) of the active compound, it is possible to add suitable polymers such as ethylcellulose and cellulose acetate.

The sterol is preferably a phytosterol or a zoosterol. Examples of phytosterols which may be mentioned are ergosterol, stigmasterol, sitoisterol, brassicasterol and campesterol. Examples of zoosterols which may be mentioned are cholesterol and lanosterol. If desired, mixtures of sterols can also be present.

Suitable basic compounds are, for example, inorganic basic salts such as ammonium carbonate and sodium carbonate, amines such as meglumine, di- or triethylamine and TRIS (2-amino-2-hydroxymethyl-1,3-propandiol) or fatty amines such as stearylamine. Stearylamine may be preferably mentioned. By the addition of basic compounds to the mixtures in the individual units, particularly stable preparations are obtained and possible discolorations are avoided.

The proportion (in percent by weight) of active compound in the individual active compound unit is advantageously 1-90%. The proportion of active compound is preferably 2-70%, particularly preferably 5-40%, in particular 10-20%. The proportion of fatty alcohol in the individual active compound unit is advantageously 10-70%, preferably 20-70%, particularly preferably 20-60% and in particular 30-60%. The proportion of triglyceride in the individual active compound unit is advantageously 10-70%, preferably 20-70%, particularly preferably 20-60% and in particular 30-60%. The proportion of fatty acid ester in the individual active compound unit is advantageously 10-70%, preferably 20-70%, particularly preferably 20-60% and in particular 30-60%. The proportion of solid paraffin is advantageously 10-70%, preferably 20-60% and in particular 30-60%. If present, the proportion of polymer in the individual active compound unit is expediently 1-25%, preferably 1-10%, particularly preferably 5-10%. If present, the proportion of sterol is expediently 1-10%, preferably 1-5%. If present, the proportion of basic compound is 0.05-5%, preferably 0.1-1%.

Preferred individual active compound units according to the invention consist of 2-70% of active compound, 10-60% of fatty alcohol, 10-60% of solid paraffin, 1-15% of polymer and 0.1-2% of a basic compound. Further preferred individual active compound units according to the invention consist of 2-70% of active compound, 10-60% of triglyceride, 10-60% of solid paraffin, 1-15% of polymer and 0.1-2% of a basic compound. Other preferred individual active compound units according to the invention consist of 2-70% of active compound, 10-60% of fatty acid ester, 10-60% of solid paraffin, 1-15% of polymer and 0.1-2% of a basic compound.

Particularly preferred individual active compound units according to the invention consist of 5-40% of active compound, 20-60% of fatty alcohol, 10-60% of solid paraffin, 1-15% of polymer and 0.1-1% of a basic compound. Further particularly preferred individual active compound units according to the invention consist of 5-40% of active compound, 20-60% of triglyceride, 10-60% of solid paraffin, 1-15% of polymer and 0.1-1% of a basic compound. Other particularly preferred individual active compound units according to the invention consists of 5-40% of active compound, 20-60% of fatty acid ester, 10-60% of solid paraffin, 1-15% of polymer and 0.1-1% of a basic compound.

Examples of active compound units according to the invention contain 5-40% of pantoprazole sodium sesquihydrate, 10-40% of cetyl alcohol, 5-60% of solid paraffin, 1-5% of polymer and 0.1-0.2% of a basic compound. Further examples of active compound units according to the invention contain 5-40% of pantoprazole sodium sesquihydrate, 10-40% of glyceryl tripalmitates, 5-60% of solid paraffin, 1-5% of polymer and 0.1-0.2% of a basic compound. Still other examples of active compound units according to the invention contain 10-20% of pantoprazole sodium sesquihydrate, 20-40% of triglyceride, 40-70% of solid paraffin, 1-5% of sterol and 0.05-0.1% of a basic compound.

The individual active compound units can be prepared, for example, by spray drying or preferably by spray solidification, in particular also by spray prilling. The preparation is particularly preferably carried out by prilling, in particular by vibration prilling. Spray drying is carried out from a suitable solvent. Suitable solvents for spray drying are preferably those in which the fatty alcohol, the triglyceride or the fatty acid ester and the solid paraffin are soluble, while the active compound is insoluble. The suitable solvents can also be solvent mixtures.

If the active compound employed is an acid-labile proton pump inhibitor, in particular a substituted pyridin-2-ylmethylsulfinyl-1H-benzimidazole, the suitable solvents are, for example, hydrocarbons, chlorinated hydrocarbons and ethyl acetate. Hydrocarbons which can be mentioned are in particular linear or branched alkanes or alternatively cycloalkanes. Examples of linear alkanes are pentane, hexane and heptane. Examples of branched alkanes which may be mentioned are 2-methylpentane and 3-methylpentane. Examples of cycloalkanes which may be mentioned are cyclohexane and cyclopentane. If desired, mixtures of the hydrocarbons such as, for example, petroleum ether can also be employed. A chlorinated hydrocarbon which may be mentioned is chloroform or, preferably, dichloromethane.

For spray drying, the fatty alcohol, the triglyceride or the fatty acid ester and the solid paraffin, and, if desired, the further pharmaceutical constituents are dissolved in the suitable solvent and the active compound is suspended therein. If desired, the active compound can also be suspended and the fatty alcohol, the triglyceride or the fatty acid ester and the solid paraffin can then be dissolved. The particle size of the active compound employed should in this case advantageously be less than 40 μm. The suspension obtained is then sprayed in a spray dryer.

Spray drying is carried out in a manner known per se. A detailed presentation of this technique is found in K. Masters, Spray Drying Handbook, 5th Ed. 1991, and J. Broadhead, S. K. Edmond Ronan, C. T. Rhodes, The Spray Drying of Pharmaceuticals, Drug Dev. Ind. Pharm. 18, 1169 (1992). The principle of spray drying consists in splitting up a solution or suspension of the product to be dried into fine droplets and drying it with a hot stream of gas. The solid component remaining after evaporation of the solvent is removed from the stream of gas by means of a cyclone and/or by a filter unit and collected.

Suitable drying gases are, in particular, air and preferably nitrogen. The gas inlet temperature depends on the solvent.

The invention further relates to a preparation comprising an acid-labile active compound, at least one fatty alcohol or at least one triglyceride or at least one fatty acid ester and at least one solid paraffin, obtainable by spray drying a suspension of the acid-labile active compound in a solution of the fatty alcohol, the triglyceride or the fatty acid ester and the solid paraffin in a suitable solvent.

The preparation of the individual active compound units is preferably carried out by spray solidification or by prilling, the preparation very particularly preferably being carried out by vibration prilling.

For spray solidification or prilling, the fatty alcohol, the triglyceride or the fatty acid ester is expediently liquefied to give a clear melt together with the solid paraffin and, if desired, further excipients. The active compound is dissolved or dispersed in this solution and the solution or dispersion obtained is sprayed or preferably prilled in a suitable device. A dispersion of the active compound in a melt of the excipients is preferably used.

Spray solidification is carried out in a manner known per se. A detailed presentation of this technique is found in P. B. Deasy, Microencapsulation and Related Drug Process (1984).

The preparation of the individual active compound units is particularly preferably carried out by solidification from the liquid phase by production of droplets by means of vibrating nozzles and by solidification of the droplets formed after stabilization thereof by drying or cooling in a suitable medium (preferably gaseous or liquid). The suitable medium can be, for example, cooled gas such as air or nitrogen. Such a process is disclosed, for example, in DE 27 25 924. The phase flowing to the nozzle is particularly preferably kept at a constant temperature here. Solidification is preferably carried out by means of sudden quenching in a suitable cooling medium. In the prilling, the liquid phase flowing to the nozzle, the vibrating nozzle and the drops formed by prilling are preferably kept, until the stabilization of their spherical form, at a constant temperature which is 1° C. to 10° C. above the melting temperature of the liquid phase, and the solidification of the drops after stabilization thereof is carried out suddenly by quenching using a gaseous or liquid cooling medium, whose operating temperature is at least 30° C. below the melting temperature of the liquid phase. Such a process and a device suitable for carrying out this process are described, for example, in EP 0 467 221 B1. For prilling by means of vibrating nozzles, suitable units are marketed, for example, by Brace GmbH, Alzenau, Germany. With the aid of prilling by means of vibrating nozzles, the individual active compound units can be obtained in the form of microspheres having a narrow monomodal particle spectrum in the particle size range from 50 μm to 2 mm. Owing to the narrow monomodal particle spectrum and a uniform, spherical form of the microspheres thus obtained, a uniformly smooth surface, a uniform, defined delivery of active compound and, with respect to the gastric passage in the case of oral administration forms (determined by the small particles), behavior like that of a solution is to be expected. The individual active compound units according to the invention thus differ from active compound-containing pellets obtained by extrusion.

In a further aspect, the invention therefore relates to microspheres comprising an acid-labile active compound and pharmaceutically acceptable excipients. The microspheres are preferably monomodal microspheres having a particle size range of 50-800 μm, preferably 50-500 μm, particularly preferably 50-400 μm, in particular of 50-200 μm. The microspheres preferably contain an acid-labile proton pump inhibitor.

The invention further relates also to microspheres comprising an acid-labile active compound and at least one fatty alcohol as a pharmaceutically acceptable excipient. In addition to the fatty alcohol, the microsphere can contain one or more further pharmaceutically suitable excipients. Examples of further suitable excipients which may be mentioned are polymers, sterols and basic compounds, the terms polymers, sterols and basic compounds having the above-mentioned meanings. In this case, the proportion (in percent by weight) of active compound in the individual active compound unit is advantageously 1-90%. The proportion of active compound is preferably 2-70%, particularly preferably 5-40%, in particular 10-20%. The proportion of fatty alcohol in the individual active compound unit is preferably 10-90%, preferably 30-85%, particularly preferably 60-80%. If present, the proportion of polymer in the individual active compound unit is expediently 1-25%, preferably 1-10%, particularly preferably 5-10%. If present, the proportion of sterol is expediently 1-10%, preferably 1-5%. If present, the proportion of basic compound is preferably 0.05-5%, preferably 0.1-1%.

They are particularly preferably microspheres obtainable by production of drops of a solution or dispersion of the acid-labile active compound in at least one fatty alcohol by means of vibrating nozzles and by solidification of the drops formed after stabilization thereof in a suitable medium. Preferably, the solution or dispersion flowing to the nozzle is kept at constant temperature.

The invention further relates to microspheres obtainable by production of drops of a solution or dispersion of the acid-labile active compound in at least one fatty alcohol, triglyceride or fatty acid ester together with at least one solid paraffin by means of vibrating nozzles and by solidification of the drops formed after stabilization thereof by cooling in a suitable medium. Preferably, the solution or dispersion flowing to the nozzle is kept at constant temperature.

The particle size of the active compound employed in the spray drying or spray solidification, prilling or vibration prilling is advantageously less than or equal to 100 μm, in particular less than 40 μm. The particle size is preferably in the range from 1-20 μm, particularly preferably in the range from 3-15 μm. Such a particle size can be achieved, for example, by grinding the active compound in a suitable mill.

The individual active compound units (preparations) according to the invention can then be used as a basis for the production of the administration forms according to the invention. Administration forms according to the invention which may be mentioned, to which the preparations can be processed, are, for example, suspensions, gels, tablets, coated tablets, multicomponent tablets, effervescent tablets, rapidly disintegrating tablets, powders in sachets, sugar-coated tablets, capsules or alternatively suppositories. Preferred administration forms here are peroral administration forms. Rapidly disintegrating tablets and effervescent tablets are particularly preferred. The excipients which are suitable for the desired administration forms are familiar to the person skilled in the art on the basis of his/her expert knowledge. In the case of peroral administration forms, it is surprisingly possible to dispense with the enteric coating.

The administration forms according to the invention contain the acid-labile active compound in the dose customary for the treatment of the respective disease. The acid-labile proton pump inhibitors according to the invention can be employed for the treatment and prevention of all the diseases which are regarded as treatable or avoidable by the use of pyridin-2-ylmethylsulfinyl-1H-benzimidazoles. In particular, such administration forms according to the invention can be employed in the treatment of stomach disorders. Such administration forms according to the invention contain between 1 and 500 mg, preferably between 5 and 60 mg, of an acid-labile proton pump inhibitor. Examples which may be mentioned are tablets or capsules which contain 10, 20, 40 or 50 mg of pantoprazole. The administration of the daily dose (e.g. 40 mg of active compound) can be carried out, for example, in the form of an individual dose or by means of a number of doses of the administration forms according to the invention (e.g. 2 times 20 mg of active compound).

The administration forms according to the invention can be combined with other medicaments, either in various combinations or in a fixed combination. In connection with the administration forms according to the invention which contain acid-labile proton pump inhibitors as active compounds, combinations with antimicrobial active compounds and combinations with NSAIDs (nonsteroidal antiinflammatory drugs) are worthy of mention. Combination with antimicrobial agents, such as are employed for the control of the microorganism *Helicobacter pylori* (*H. pylori*), may particularly be mentioned.

Examples of suitable antimicrobial active compounds (active against *Helicobacter pylori*) are described in EP-A-0 282 131. Examples of antimicrobial agents suitable for the control of the microorganism *Helicobacter pylori* which may be mentioned are, for example, bismuth salts [e.g. bismuth subcitrate, bismuth subsalicylate, ammonium bismuth(III) potassium citrate dihydroxide, bismuth nitrate oxide, dibismuth tris(tetraoxodialuminate)], but in particular β-lactam antibiotics, for example penicillins (such as benzylpenicillin, phenoxymethylpenicillin, propicillin, azidocillin, dicloxacillin, flucloxacillin, oxacillin, amoxicillin, bacampicillin, ampicillin, meziocillin, piperacillin or aziocillin), cephalosporins (such as cefadroxil, cefaclor, cefalexin, cefixime, cefuroxime, cefetamet, cefadroxil, ceftibuten, cefpodoxime, cefotetan, cefazolin, cefoperazon, ceftizoxime, cefotaxime, ceftazidime, cefamandol, cefepime, cefoxitin, cefodizime, cefsulodin, ceftriaxon, cefotiam or cefmenoxime) or other β-lactam antibiotics (e.g. aztreonam, loracarbef or meropenem); enzyme inhibitors, for example sulbactam; tetracyclines, for example tetracycline, oxytetracycline, minocycline or doxycycline; aminoglycosides, for example tobramycin, gentamicin, neomycin, streptomycin, amikacin, netilmicin, paromomycin or spectinomycin; amphenicols, for example chloramphenicol or thiamphenicol; lincomycins and macrolide antibiotics, for example clindamycin, lincomycin, erythromycin, clarithromycin, spiramycin, roxithromycin or azithromycin: polypeptide antibiotics, for example colistin, polymixin B, teicoplanin or vancomycin; gyrase inhibitors, for example norfloxacin, cinoxacin, ciprofloxacin, pipemidic acid, enoxacin, nalidixic acid, pefloxacin. fleroxacin or ofloxacin; nitroimidazoles, for example metronidazole; or other antibiotics, for example fosfomycin or fusidic acid. Particularly worthy of mention in this connection is the administration of an acid-labile proton pump inhibitor with the combination of a multiplicity of antimicrobial active compounds, for example with the combination of a bismuth salt and/or tetracyclines with metronidazole or the combination of amoxicillin or clarithromycin with metronidazole and amoxicillin with clarithromycin.

The production of administration forms and preparations according to the invention is described by way of example below. The following examples illustrate the invention in greater detail, without restricting it.

EXAMPLES

Production of the Preparations

Example 1

50 g of solid paraffin, 34.9 g of cetyl alcohol and 0.1 g of stearylamine are fused to give a clear mixture. 5.0 g of povidone are dissolved in the clear melt. 10.0 g of pantoprazole sodium sesquihydrate are added and homogeneously suspended at a temperature of 56-60° C. The suspension is prilled in the molten state and the drops thus formed are solidified in a cooling zone.

Example 2

55 g of solid paraffin, 30.9 g of cetyl alcohol and 0.1 g of stearylamine are fused to give a clear mixture. 4.0 g of povidone are dissolved in the clear melt. 10.0 g of pantoprazole-magnesium are added and homogeneously suspended at a temperature of 56-60° C. The suspension is prilled in the molten state and the drops thus resulting are solidified in a cooling zone.

Example 3

45.0 g of solid paraffin, 33.8 g of cetyl alcohol, 1.0 g of β-sitosterol and 0.2 g of stearylamine are fused to give a clear mixture. 1.0 g of povidone and 4.0 g of ethylcellulose are dissolved in the clear melt. 15.0 g of pantoprazole sodium sesquihydrate are added and homogeneously suspended at a temperature of 56-60° C. The suspension is prilled in the molten state and the drops thus resulting are solidified in a cooling zone.

Example 4

52.0 g of solid paraffin, 30.3 g of cetyl alcohol and 0.2 g of stearylamine are fused to give a clear mixture. 5.0 g of povidone are dissolved in the clear melt. 12.5 g of pantoprazole sodium sesquihydrate are added and homogeneously suspended at a temperature of 56-60° C. The suspension is prilled in the molten state and the drops thus formed are solidified in a cooling zone.

Example 5

77.2 g of cetyl alcohol and 0.3 g of stearylamine are fused to give a clear mixture. 10.0 g of povidone are dissolved in the clear mixture. 12.5 g of pantoprazole sodium sesquihydrate are added and homogeneously suspended at a temperature of 56-60° C. The suspension is prilled in the molten state and the drops thus formed are solidified in a cooling zone.

Example 6

47 g of solid paraffin, 40 g of glyceryl tripalmitate (Dynasan 116, Hüls), and 3 g of sitosterol are fused to give a clear mixture at 100° C. and cooled to 55-60° C. 10 g of lansoprazole are added and homogeneously suspended. The suspension is added to the feed container of a prilling unit (Brace) and prilled at about 0.1 bar from a 200 µm nozzle. A periodic oscillation of the frequency of about 390 Hz is transmitted to the nozzle head in the course of this. The resulting drops are solidified in a cooling zone using air with a temperature of −30° C.

Example 7

15 g of glyceryl trimyristate (Dynasan 114), 15 grams of glyceryl tripalmitate (Dynasan 116), 50 grams of solid paraffin and 5 g of cholesterol are fused to give a clear mixture at about 100° C. The clear melt is cooled to about 55-65° C. 15 g of rabeprazole are added, the compound is distributed uniformly and the homogeneous suspension is prilled as in Example 6.

Example 8

10 g of glyceryl tripalmitate (Dynasan 116), 20 g of glyceryl trimyristate (Dynasan 114), 52 g of solid paraffin and 3 g of sitosterol are fused to give a clear mixture at about 100° C. The clear melt is cooled to 55-65° C. 15 g of omeprazole Mg are added and homogeneously suspended. The suspension is added to the feed container of a prilling unit (Brace) and prilled at 90 mbar by means of a 200 µm nozzle. A periodic oscillation of the frequency of about 400 Hz is transmitted to the nozzle head in the course of this. The resulting drops are solidified in a cooling zone using air with a temperature of −30° C.

Example 9

18 g of tristearate, 60 g of solid paraffin and 5 g of cholesterol are fused to give a clear mixture. The clear melt is cooled to 56-60° C. 10 g of pantoprazole sodium sesquihydrate are introduced and this is homogeneously dispersed. The suspension is prilled in the molten state in a prilling unit (Brace) having vibrating nozzles and the resulting drops are solidified in a cooling zone.

Example 10

18 g of cetyl palmitate, 40 g of solid paraffin and 2 g of cholesterol are fused to give a clear mixture. The clear melt is cooled to 56-60° C. 10 g of pantoprazole sodium sesquihydrate are introduced and homogenized until a uniform suspension is formed. The liquid suspension is prilled in the molten state in a prilling unit (Brace) having vibrating nozzles and the resulting drops are solidified in a cooling zone.

Example 11

50 g of solid paraffin and 40 g of cetyl palmitate (Cutina® CP) are fused to give a clear mixture at 100° C. The clear melt is cooled to 50-60° C. 10 g of pantoprazole sodium sesquihydrate are introduced and homogeneously suspended. The liquid suspension is prilled in the molten state in a prilling unit (Brace) having vibrating nozzles (200 µm nozzle) and the resulting drops are solidified in a cooling zone.

Example 12

50 g of solid paraffin and 40 g of cetyl alcohol are fused to give a clear mixture at 100° C. The clear melt is cooled to 50-60° C. 10 g of pantoprazole sodium sesquihydrate are introduced and homogeneously suspended. The liquid suspension is prilled in the molten state in a prilling unit (Brace) having vibrating nozzles (200 µm nozzle) and the resulting drops are solidified in a cooling zone.

Example 13

50 g of solid paraffin and 40 g of glyceryl trimyristate are fused to give a clear mixture at 100° C. The clear melt is cooled to 50-60° C. 10 g of pantoprazole sodium sesquihydrate are introduced and homogeneously suspended. The liquid suspension is prilled in the molten state in a prilling unit (Brace) having vibrating nozzles (200 µm nozzle) and the resulting drops are solidified in a cooling zone.

Example 14

47 g of solid paraffin, 40 g of glyceryl tripalmitate (Dynasan 116, Hüls) and 3 g of sitosterol are fused to give a clear mixture at 100° C. and cooled to 55-60° C. 10 g of lansoprazole are added and homogeneously suspended. The suspension is added to the feed container of a prilling unit (Brace) and prilled at about 0.1 bar from a 200 µm nozzle. A periodic oscillation of the frequency of about 390 Hz is transmitted to the nozzle head in the course of this. The resulting drops are solidified in a cooling zone using air with a temperature of −30° C.

Example 15

30 g of tristearate, 60 g of solid paraffin, 4 g of sitosterol and 0.07 g of stearylamine are fused to give a clear mixture. The clear melt is cooled to 56-60° C. 15 g of pantoprazole sodium sesquihydrate are introduced and this is homogeneously dispersed. The suspension is prilled in the molten state in a prilling unit (Brace) having vibrating nozzles and the resulting drops are solidified in a cooling zone.

The preparations obtained according to Examples 1-15 have a particle size in the range 50-700 µm. By variation of the process conditions it is possible, for example, to obtain larger particles.

Preparation of the Administration Forms

Example A 134.7 g of mannitol, 30 g of Kollidon® 30 and 20 g of xanthan are mixed in dry form. The mixture is granulated in a fluidized bed granulator using water. Granules having a particle size of 0.8-1.5 mm are obtained, which are mixed with the preparation (125 g) obtained according to Example 1. The mixture thus obtained is dispensed into sachets or compressed to give tablets—if desired together with further tablet excipients—in a manner known to the person skilled in the art.

Example B

An amount of the preparation obtained according to Example 2 corresponding to 22.6 mg of pantoprazole magnesium is mixed with 500 mg of lactose and 100 mg of xanthan. Depending on individual sense of taste, the mixture is additionally mixed with flavorings (sweetener, aroma) and then dispensed into a sachet. By dissolving the contents of a sachet in a glass of water with stirring, a suspension for oral administration is obtained.

Example C

An amount of the preparation from Example 3 corresponding to 45.2 mg of pantoprazole sodium sesquihydrate is mixed with the corresponding amount of lactose. This mixture is mixed with a mixture of citric acid and sodium carbonate. After addition of a suitable lubricant (e.g. sodium stearyl fumarate) and addition of one or more suitable flavorings, the mixture obtained is compressed directly (without further granulation) to give an effervescent tablet. By dissolving a tablet in a glass of water, a suspension for oral administration is obtained.

Example D

An amount of the preparation according to Example 4 corresponding to 45.2 mg of pantoprazole sodium sesquihydrate is mixed with lactose to improve the flow properties. The mixture is dispensed into hard gelatin capsules of suitable size together with other suitable active compounds (e.g. amoxicillin or NSAIDs in customary dose forms).

Example E 300 mg of lactose are added to an amount of the preparation according to Example 6 comprising 30 mg of lansoprazole. The two components are mixed with citric acid and sodium carbonate and, after addition of a suitable lubricant (e.g. sodium stearyl fumarate) and addition of suitable flavorings, compressed to give a tablet.

Example F 450 mg of sucrose and 300 mg of xanthan are added to an amount of the preparation according to Example 7 corresponding to 30 mg of rabeprazole. The components are mixed and treated with flavor corrigents. The granules are filled into sachets. The contents of a sachet can be added to a glass of water and, after stirring, are ready for use.

Example G 60 grams of the preparation according to Example 8 are mixed in dry form with 140 grams of mannitol, 30 grams of Kollidon 30 and 20 grams of xanthan. The mixture is granulated with water in a fluidized bed granulator. Granules are obtained with the particle size 0.8-1.5 mm. The mixture thus obtained is dispensed into sachets.

The invention claimed is:

1. An oral solid active compound unit comprising a solidified drop, the solidified drop comprising:
   a matrix comprising a mixture of cetyl palmitate or at least one triglyceride selected from the group consisting of tristearate, tripalmitate and trimyristate, and at least one solid paraffin; and
   an acid-labile active compound selected from the group consisting of substituted pyridin-2-yl-methylsulfinyl-1H-benzimidazoles, substituted phenylmethylsulfinyl-1H-benzimidazoles, substituted cycloheptapyridin-9-ylsulfinyl-1H-benzimidazoles and substituted pyridin-2-ylmethylsulfinyl-thienoimidazoles, wherein said acid-labile active compound is present in said matrix, and wherein the solidified drop does not comprise an enteric coating.

2. The oral solid active compound unit as claimed in claim 1, wherein the matrix further comprises one or more excipients selected from the group consisting of polymers, sterols and basic compounds.

3. The oral solid active compound unit as claimed in claim 1, wherein the acid-labile active compound is selected from the group consisting of omeprazole, pantoprazole, lansoprazole and rabeprazole.

4. The oral solid active compound unit as claimed in claim 1, wherein the acid-labile active compound is pantoprazole sodium sesquihydrate, (−)-pantoprazole sodium sesquihydrate, omeprazole magnesium, omeprazole, esomeprazole magnesium or esomeprazole.

5. The oral solid active compound unit as claimed in claim 1, wherein the acid-labile active compound is pure enantiomer.

6. The oral solid active compound unit as claimed in claim 1, wherein the acid-labile active compound is esomeprazole or (−)-pantoprazole.

7. The oral solid active compound unit as claimed in claim 1, wherein the solidified drop has a particle size range of 50-800 μm.

8. The oral solid active compound unit as claimed in claim 1, wherein the solidified drop has a particle size range of 50-400 μm.

9. The oral solid active compound unit as claimed in claim 1, wherein the solidified drop has a particle size range of 50-200 μm.

10. The oral solid active compound unit as claimed in claim 1, wherein the solid paraffin is paraffinum solidum or ozocerite.

11. The oral solid active compound unit as claimed in claim 1, wherein the acid-labile active compound is 1-90% by weight of the oral solid active compound unit.

12. The oral solid active compound unit as claimed in claim 11, wherein the acid-labile active compound is 2-70% by weight of the oral solid active compound unit.

13. The oral solid active compound unit as claimed in claim 11, wherein the acid-labile active compound is 5-40% by weight of the oral solid active compound unit.

14. The oral solid active compound unit as claimed in claim 11, wherein the acid-labile active compound is 10-20% by weight of the oral solid active compound unit.

15. The oral solid active compound unit as claimed in claim 1, wherein the solid paraffin is 10-70% by weight of the oral solid active compound unit.

16. The oral solid active compound unit as claimed in claim 15, wherein the solid paraffin is 30-60% by weight of the oral solid active compound unit.

17. The oral solid active compound unit as claimed in claim 15, wherein the solid paraffin is 20-60% by weight of the oral solid active compound unit.

18. The oral solid active compound unit as claimed in claim 1, wherein the acid-labile active compound is selected from the group consisting of 5-methoxy-2-[(4-methoxy-3,5-dimethyl-2-pyridinyl)methylsulfinyl)-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methylsulfinyl]-1H-benzimidazole (INN: lansoprazole), 2-([4-(3-methoxypropoxy)-3-methylpyridin-2-yl]-methylsulfinyl)-1H-benzimidazole (INN: rabeprazole), 2-[2-(N-isobutyl-N-methylamino)benzylsulfinyl]benzimidazole (INN: leminoprazole), 2-(4-methoxy-6,7,8,9-tetrahydro-5H-cyclohepta-[b]-pyridin-9-ylsulfinyl)-1H-benzimidazole (INN: nepaprazole), 5-methoxy-2-[(S)-[(4-methoxy-3,5-dimethyl-2-pyridinyl)methyl]sulfinyl]-1H-benzimidazole (INN: esomeprazole), (−)-pantoprazole, pantoprazole sodium sesquihydrate, (−)-pantoprazole sodium sesquihydrate, omeprazole magnesium, omeprazole, esomeprazole magnesium and esomeprazole.

* * * * *